(12) United States Patent
Mann et al.

(10) Patent No.: US 9,854,801 B2
(45) Date of Patent: Jan. 2, 2018

(54) WEED CONTROL FROM APPLICATIONS OF AN ETHYLENE INHIBITOR AND A PYRIDINE CARBOXYLIC ACID HERBICIDE

(71) Applicant: Dow AgroSciences LLC, Indianapolis, IN (US)

(72) Inventors: Richard K. Mann, Franklin, IN (US); Carla N. Yerkes, Crawfordsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/282,449

(22) Filed: Sep. 30, 2016

(65) Prior Publication Data

US 2017/0094970 A1    Apr. 6, 2017

Related U.S. Application Data

(60) Provisional application No. 62/235,847, filed on Oct. 1, 2015.

(51) Int. Cl.
*A01N 43/40* (2006.01)
*A01N 27/00* (2006.01)

(52) U.S. Cl.
CPC ............ *A01N 43/40* (2013.01); *A01N 27/00* (2013.01)

(58) Field of Classification Search
None
See application file for complete search history.

(56) References Cited

U.S. PATENT DOCUMENTS

| | | |
|---|---|---|
| 2008/0039322 A1 | 2/2008 | Wang et al. |
| 2010/0144533 A1 | 6/2010 | Baier et al. |
| 2012/0065067 A1 | 3/2012 | Larsen et al. |

*Primary Examiner* — Alton Pryor
(74) *Attorney, Agent, or Firm* — Michael R. Asam; Meunier Carlin & Curfman, LLC

(57) ABSTRACT

Disclosed herein are herbicidal compositions comprising a herbicidal effective amount of (a) an ethylene inhibitor, and (b) a compound defined by Formula (I), or an agriculturally acceptable salt or ester thereof:

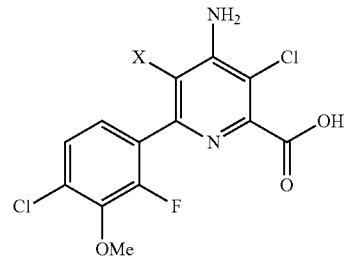

Formula (I)

wherein X is hydrogen or fluorine. The ethylene inhibitor can be 1-methylcyclopropene. The weight ratio of 1-methylcyclopropene, in g ai/ha to the compound defined by Formula (I), or an agriculturally acceptable salt or ester thereof, in g ai/ha can be from 1:1000 to 400:1. Also disclosed herein are methods of controlling undesirable vegetation which comprise applying to vegetation or an area adjacent the vegetation or applying to soil or water to limit the emergence or growth of vegetation the composition described above.

20 Claims, No Drawings

WEED CONTROL FROM APPLICATIONS OF AN ETHYLENE INHIBITOR AND A PYRIDINE CARBOXYLIC ACID HERBICIDE

CROSS REFERENCE TO RELATED APPLICATIONS

The present application claims priority to U.S. Patent Application No. 62/235,847, filed Oct. 1, 2015, which application is incorporated herein fully by this reference.

FIELD OF THE DISCLOSURE

The present disclosure relates to herbicidal compositions comprising a herbicidally effective amount of (a) an ethylene inhibitor (e.g., 1-methylcyclopropene) and (b) a 2-arylpyridine carboxylic acid, or an agriculturally acceptable salt or ester thereof. The present disclosure also relates to methods for controlling undesirable vegetation.

BACKGROUND

Many recurring problems in agriculture involve controlling the growth of undesirable vegetation that can, for instance, negatively affect the growth and yield of desirable vegetation. To help control undesirable vegetation, researchers have produced a variety of chemicals and chemical formulations effective in controlling such unwanted growth. However, a continuing need exists for new methods to control growth of undesirable vegetation, including volunteer crops. This has particularly become a problem as more volunteer crops are herbicide tolerant, thereby making them more difficult to eradicate.

SUMMARY OF THE DISCLOSURE

Herbicidal compositions are described herein. The herbicidal composition can comprise an ethylene inhibitor and a compound defined by Formula (I), or an agriculturally acceptable salt or ester thereof:

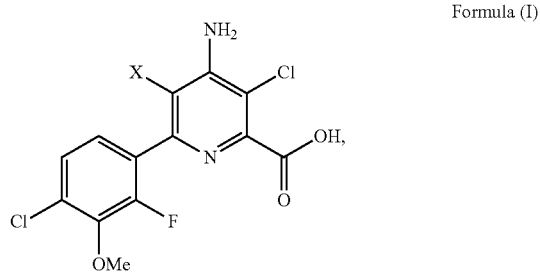

Formula (I)

wherein X is hydrogen or fluorine. The ethylene inhibitor and the compound of Formula I can be provided in a synergistic, herbicidally effective amount.

The ethylene inhibitor can be 1-methylcyclopropene. In some embodiments, the composition can comprise 1-methylcyclopropene and the compound defined by Formula (I), or an agriculturally acceptable salt or ester thereof. The weight ratio of 1-methylcyclopropene, in g ai/ha to the compound defined by Formula (I), or an agriculturally acceptable salt or ester thereof, in g ai/ha can be from 1:1000 to 400:1. In some embodiments, the weight ratio of 1-methylcyclopropene, in g ai/ha to the compound defined by Formula (I), or an agriculturally acceptable salt or ester thereof, in g ai/ha can be from 1:60 to 50:1, for example 1:16 to 2.5:1. The ethylene inhibitor, for example 1-methylcyclopropene, can be applied at a rate of 0.1 g ai/ha to 100 g ai/ha, for example, 2 g ai/ha to 20 g ai/ha. The compound of Formula I can be applied at a rate of 0.25 g ai/ha to 100 g ai/ha, for example, 8 g ai/ha to 32 g ai/ha.

The composition can further comprise an additional herbicide, a pesticide, an insecticide, a fungicide, a herbicidal safener, an RNAi, an agriculturally acceptable adjuvant or carrier, or combinations thereof. In some embodiments, the active ingredients in the herbicidal composition consist of the ethylene inhibitor and the compound defined by Formula (I), or an agriculturally acceptable salt or ester thereof.

Methods of controlling undesirable vegetation are described herein. The method can include applying a composition as described herein to vegetation or an area adjacent the vegetation or applying to soil or water to control the emergence or growth of vegetation. The active agents in the composition can be applied simultaneously or sequentially.

In some embodiments, the composition can be applied postemergence to the undesirable vegetation. The undesirable vegetation can include a grass weed, a broadleaf weed, a sedge weed, or a combination thereof. For example, the undesirable vegetation can include a weed from the genus *Cyperus, Echinochloa, Digitaria,* or *Ipomoea,* such as *Echinochloa crus-galli* (barnyard grass), *Digitaria sanguinalis* (large crabgrass), *Cypress* spp. (annual or perennial sedge), or *Ipomoeae hederacea* (morning glory). The undesirable vegetation may be controlled in monocot crops, including but not limited to rice, wheat, barley, oats, corn, maize, *sorghum*, milo, *Brachiaria*, pastures, sugarcane and turfgrass. In some embodiments, the undesirable vegetation is controlled in a genetically modified crop that may have herbicidal tolerance or resistance. The undesirable vegetation can be controlled in vegetables, soybeans, cotton, sunflower, canola, oilseed, rapeseed, tree and vine crops, perennial crops, and plantation crops. The undesirable vegetation can also be controlled in non-crop areas such as roadsides, industrial vegetation management, forests, turfgrass, golf courses, parks, cemeteries, athletic fields, and sod farms.

Methods for modifying crop growth and yields are also disclosed herein. In some embodiments, crop growth and yield may be modified in crops such as soybeans, cotton, sunflower, canola, oilseed rapeseed, rice, wheat, barley, oats, corn, maize, *sorghum*, milo, *Brachiaria*, pastures, sugarcane, turfgrass, tree and vine crops, perennial crops, and plantation crops.

DETAILED DESCRIPTION

The present disclosure relates to herbicidal compositions comprising a synergistic herbicidally effective amount of (a) an ethylene inhibitor (e.g. 1-methylcyclopropene), and (b) a 2-arylpyridine carboxylic acid, or an agriculturally acceptable salt or ester thereof. The present disclosure also relates to methods for controlling undesirable vegetation.

Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the terms "herbicide" and "herbicidal active ingredient" refer to an active ingredient that kills, controls, or otherwise adversely modifies the growth and development of vegetation, particularly undesirable vegetation, such as weeds, volunteer crops, and other plant species that differ from the plant species intended for growth, when applied in an appropriate amount.

As used herein, a herbicidally effective amount" refers to an amount of an active ingredient that causes a "herbicidal effect," i.e., an adversely modifying effect including, for instance, a deviation from natural growth or development, killing, necrosis, stunting, regulation, desiccation, and retardation.

As used herein, "applying a herbicide or herbicidal composition" refers to delivering the herbicide or herbicidal composition directly to the targeted vegetation or to the locus thereof or to the area where control of undesired vegetation is desired. Methods of application include, but are not limited to pre-emergently contacting soil or water, and post-emergently contacting the undesirable vegetation or an area adjacent to the undesirable vegetation.

As used herein, the terms "crops" and "vegetation" can include, for instance, dormant seeds, germinant seeds, emerging seedlings, plants emerging from vegetative propagules, immature vegetation, and established vegetation.

Compositions and methods of the present disclosure can include an ethylene inhibitor and a 2-arylpyridine carboxylic acid or an agriculturally acceptable salt or ester thereof.

Ethylene acts throughout the life of a plant by stimulating or regulating various processes such as ripening, opening of flowers, and shedding of leaves. In some embodiments, the composition can include an ethylene inhibitor. The ethylene inhibitor can be selected from the group consisting of 1-methylcyclopropene, silver (I), aminoethoxyvinylglycine (AVG), nitric oxide, trans-cyclooctene, 1-aminocyclopropane-1-carboxylic acid (ACC) synthase inhibitor, ACC oxidase, of agriculturally acceptable salts and esters thereof, and combinations thereof.

In certain embodiments, the ethylene inhibitor can include 1-methylcyclopropene. 1-methylcyclopropene is a cyclopropene derivative used as a synthetic plant growth regulator. 1-methylcyclopropene can inhibit ethylene by tightly binding to ethylene receptors, thereby blocking the effects of ethylene in plants. 1-methylcyclopropene is or has been commercially available, for example, under CAS No. 3100-04-7 by Rely Chemicals and Capot Chemical Co., Ltd.

The ethylene inhibitor (e.g., 1-methylcyclopropene) can be applied to vegetation or an area adjacent the vegetation or applied to soil or water to limit the emergence or growth of vegetation in an amount sufficient to induce a herbicidal effect. In some embodiments, the ethylene inhibitor is applied to vegetation or an area adjacent the vegetation or applied to soil or water to limit the emergence or growth of vegetation in an amount of 0.1 grams or greater of active ingredient per hectare (g ai/ha) (e.g., 0.2 g ai/ha or greater, 0.3 g ai/ha or greater, 0.4 g ai/ha or greater, 0.5 g ai/ha or greater, 0.6 g ai/ha or greater, 0.7 g ai/ha or greater, 0.8 g ai/ha or greater, 0.9 g ai/ha or greater, 1 g ai/ha or greater, 1.1 g ai/ha or greater, 1.2 g ai/ha or greater, 1.3 g ai/ha or greater, 1.4 g ai/ha or greater, 1.5 g ai/ha or greater, 1.6 g ai/ha or greater, 1.7 g ai/ha or greater, 1.8 g ai/ha or greater, 1.9 g ai/ha or greater, 2 g ai/ha or greater, 2.25 g ai/ha or greater, 2.5 g ai/ha or greater, 2.75 g ai/ha or greater, 3 g ai/ha or greater, 4 g ai/ha or greater, 5 g ai/ha or greater, 6 g ai/ha or greater, 7 g ai/ha or greater, 8 g ai/ha or greater, 9 g ai/ha or greater, 10 g ai/ha or greater, 11 g ai/ha or greater, 12 g ai/ha or greater, 13 g ai/ha or greater, 14 g ai/ha or greater, 15 g ai/ha or greater, 16 g ai/ha or greater, 17 g ai/ha or greater, 18 g ai/ha or greater, 19 g ai/ha or greater, 20 g ai/ha or greater, 21 g ai/ha or greater, 22 g ai/ha or greater, 23 g ai/ha or greater, 24 g ai/ha or greater, 25 g ai/ha or greater, 26 g ai/ha or greater, 27 g ai/ha or greater, 28 g ai/ha or greater, 29 g ai/ha or greater, 30 g ai/ha or greater, 31 g ai/ha or greater, 32 g ai/ha or greater, 33 g ai/ha or greater, 34 g ai/ha or greater, 35 g ai/ha or greater, 36 g ai/ha or greater, 37 g ai/ha or greater, 38 g ai/ha or greater, 39 g ai/ha or greater, 40 g ai/ha or greater, 41 g ai/ha or greater, 42 g ai/ha or greater, 43 g ai/ha or greater, 44 g ai/ha or greater, 45 g ai/ha or greater, 46 g ai/ha or greater, 47 g ai/ha or greater, 48 g ai/ha or greater, 49 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, 95 g ai/ha or greater, 100 g ai/ha or greater, 110 g ai/ha or greater, 120 g ai/ha or greater, 130 g ai/ha or greater, 140 g ai/ha or greater, 150 g ai/ha or greater, 160 g ai/ha or greater, 170 g ai/ha or greater, 180 g ai/ha or greater, 190 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, or 290 g ai/ha or greater).

In some embodiments, the ethylene inhibitor is applied to vegetation or an area adjacent the vegetation or applied to soil or water to limit the emergence or growth of vegetation in an amount of 300 g ai/ha or less (e.g., 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, 6 g ai/ha or less, 5 g ai/ha or less, 4 g ai/ha or less, 3 g ai/ha or less, 2.75 g ai/ha or less, 2.5 g ai/ha or less, 2.25 g ai/ha or less, 2 g ai/ha or less, 1.9 g ai/ha or less, 1.8 g ai/ha or less, 1.7 g ai/ha or less, 1.6 g ai/ha or less, 1.5 g ai/ha or less, 1.4 g ai/ha or less, 1.3 g ai/ha or less, 1.2 g ai/ha or less, 1.1 g ai/ha or less, 1 g ai/ha or less, 0.9 g ai/ha or less, 0.8 g ai/ha or less, 0.7 g ai/ha or less, 0.6 g ai/ha or less, 0.5 g ai/ha or less, 0.4 g ai/ha or less, 0.3 g ai/ha or less, or 0.2 g ai/ha or less).

The ethylene inhibitor can be applied to vegetation or an area adjacent the vegetation or applied to soil or water to limit the emergence or growth of vegetation in an amount ranging from any of the minimum values described above to any of the maximum values described above. In some embodiments, the ethylene inhibitor is applied to vegetation or an area adjacent the vegetation or applied to soil or water to limit the emergence or growth of vegetation in an amount of from 0.1-300 g ai/ha (e.g., from 0.1-5 g ai/ha, from 2.5-40 g ai/ha, from 0.1-40 g ai/ha, from 1-50 g ai/ha, from 5-75 g ai/ha, from 5-40 g ai/ha, from 5-20 g ai/ha, or from 2-20 g ai/ha). In some embodiments, the ethylene inhibitor is applied in an amount from 0.1-100 g ai/ha.

In addition to the ethylene inhibitor, the compositions described herein include a 2-arylpyridine carboxylic acid, an agriculturally acceptable salt or ester thereof as defined by Formula (I):

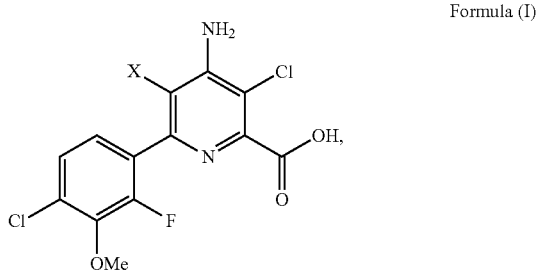

Formula (I)

wherein X is hydrogen or a halogen.

In some embodiments, the compound of Formula (I) can be defined by a compound of Formula (II) or Formula (III) (also known as halauxifen), or its salts or esters:

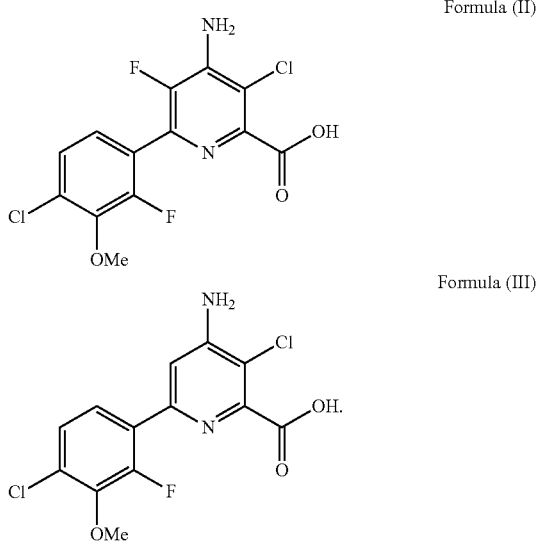

Formula (II)

Formula (III)

The compounds represented in Formula I and agriculturally acceptable salts and esters thereof, are synthetic herbicides that can be used for a broad spectrum of weed control. The herbicidal activity of the 2-arylpyridine carboxylic acids are described in U.S. Publication No. 2014/0274715 to Schmitzer et al. Methods of making and using these compounds are known in the art. See, e.g., U.S. Pat. No. 7,314,849 to Balko et al., U.S. Pat. No. 7,538,214 to Epp et al., and U.S. Publication No. 2014/0274715 to Schmitzer et al.

The compounds of Formula I can be provided in their acid forms, or as agriculturally acceptable salts or esters thereof. Exemplary agriculturally acceptable salts of Formula (I) include, but are not limited to, sodium salts, potassium salts, ammonium salts or substituted ammonium salts, in particular mono-, di-, and tri-C1-C8-alkylammonium salts such as methylammonium, dimethylammonium, triethylammonium, and isopropylammonium, mono-, di- and tri-hydroxy-C2-C8-alkylammonium salts such as hydroxyethylammonium, di(hydroxyethyl)ammonium, tri(hydroxyethyl) ammonium, hydroxypropylammonium, di(hydroxypropyl) ammonium and tri(hydroxypropyl)ammonium salts, triisopropanolammonium salts, choline salts, olamine salts, and diglycolamine salts.

Exemplary agriculturally acceptable esters of Formula (I) include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, pentyl, hexyl, heptyl, isoheptyl, isooctyl, butotyl, 2-ethylhexyl and butoxyethyl esters, and aryl esters such as benzyl. Exemplary agriculturally acceptable esters include the methyl ester of 4-amino-3-chloro-6-(4-chloro-2-fluoro-3-methoxyphenyl)pyridine-2-carboxylic acid and the benzyl ester of 4-amino-3-chloro-5-fluoro-6-(4-chloro-2-fluoro-3-methoxyphenyl)pyridine-2-carboxylic acid.

The compounds represented by Formula (I) or an agriculturally acceptable salt or ester thereof, can be applied to vegetation or an area adjacent the vegetation or applied to soil or water to limit the emergence or growth of vegetation in an amount sufficient to induce a herbicidal effect. In some embodiments, the compounds represented by Formula (I) or an agriculturally acceptable salt or ester thereof, is applied to vegetation or an area adjacent the vegetation or applied to soil or water to limit the emergence or growth of vegetation in an amount of 0.1 grams or greater of active ingredient per hectare (g ai/ha) (e.g., 0.2 g ai/ha or greater, 0.3 g ai/ha or greater, 0.4 g ai/ha or greater, 0.5 g ai/ha or greater, 0.6 g ai/ha or greater, 0.7 g ai/ha or greater, 0.8 g ai/ha or greater, 0.9 g ai/ha or greater, 1 g ai/ha or greater, 1.1 g ai/ha or greater, 1.2 g ai/ha or greater, 1.3 g ai/ha or greater, 1.4 g ai/ha or greater, 1.5 g ai/ha or greater, 1.6 g ai/ha or greater, 1.7 g ai/ha or greater, 1.8 g ai/ha or greater, 1.9 g ai/ha or greater, 2 g ai/ha or greater, 2.25 g ai/ha or greater, 2.5 g ai/ha or greater, 2.75 g ai/ha or greater, 3 g ai/ha or greater, 4 g ai/ha or greater, 5 g ai/ha or greater, 6 g ai/ha or greater, 7 g ai/ha or greater, 8 g ai/ha or greater, 9 g ai/ha or greater, 10 g ai/ha or greater, 11 g ai/ha or greater, 12 g ai/ha or greater, 13 g ai/ha or greater, 14 g ai/ha or greater, 15 g ai/ha or greater, 16 g ai/ha or greater, 17 g ai/ha or greater, 18 g ai/ha or greater, 19 g ai/ha or greater, 20 g ai/ha or greater, 21 g ai/ha or greater, 22 g ai/ha or greater, 23 g ai/ha or greater, 24 g ai/ha or greater, 25 g ai/ha or greater, 26 g ai/ha or greater, 27 g ai/ha or greater, 28 g ai/ha or greater, 29 g ai/ha or greater, 30 g ai/ha or greater, 31 g ai/ha or greater, 32 g ai/ha or greater, 33 g ai/ha or greater, 34 g ai/ha or greater, 35 g ai/ha or greater, 36 g ai/ha or greater, 37 g ai/ha or greater, 38 g ai/ha or greater, 39 g ai/ha or greater, 40 g ai/ha or greater, 41 g ai/ha or greater, 42 g ai/ha or greater, 43 g ai/ha or greater, 44 g ai/ha or greater, 45 g ai/ha or greater, 46 g ai/ha or greater, 47 g ai/ha or greater, 48 g ai/ha or greater, 49 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, or 95 g ai/ha or greater).

In some embodiments, the compound represented by Formula (I) or an agriculturally acceptable salt or ester thereof, is applied to vegetation or an area adjacent the vegetation or applied to soil or water to limit the emergence or growth of vegetation in an amount of 100 g ai/ha or less (e.g., 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, 6 g ai/ha or less, 5 g ai/ha or less, 4 g ai/ha or less, 3 g ai/ha or less, 2.75 g ai/ha or less, 2.5 g ai/ha or less, 2.25 g ai/ha or less, 2 g ai/ha or less, 1.9 g ai/ha or less, 1.8 g ai/ha or less, 1.7 g ai/ha or less, 1.6 g ai/ha or less, 1.5 g ai/ha or less, 1.4 g ai/ha or less, 1.3 g ai/ha or less, 1.2 g ai/ha or less, 1.1 g ai/ha or less, 1 g ai/ha or less, 0.9 g ai/ha or less, 0.8 g ai/ha or less, 0.7 g ai/ha or less, 0.6 g ai/ha or less, 0.5 g ai/ha or less, 0.4 g ai/ha or less, 0.3 g ai/ha or less, or 0.25 g ai/ha or less).

The compound represented by Formula (I) or an agriculturally acceptable salt or ester thereof, can be applied to vegetation or an area adjacent the vegetation or applied to soil or water to limit the emergence or growth of vegetation in an amount ranging from any of the minimum values described above to any of the maximum values described above. In some embodiments, the compound represented by Formula (I) or an agriculturally acceptable salt or ester thereof, is applied to vegetation or an area adjacent the vegetation or applied to soil or water to limit the emergence or growth of vegetation in an amount of from 0.1-100 g ai/ha (e.g., from 0.1-5 g ai/ha, from 2.5-40 g ai/ha, from 0.1-40 g ai/ha, from 1-60 g ai/ha, from 2-100 g ai/ha, from 5-100 g ai/ha, from 5-75 g ai/ha, from 5-40 g ai/ha, or from 8-32 g ai/ha). In some embodiments, the compound represented by Formula I or an agriculturally acceptable salt or ester thereof, is applied in an amount from 0.25-100 g ai/ha.

The herbicidal composition can contain (a) an ethylene inhibitor mixed with or applied in combination with (b) a compound represented by Formula (I) or an agriculturally acceptable salt or ester thereof. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the Herbicide Handbook of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E=X+Y-(X*Y)/100$$

wherein

X=effect in percent using (a) compound represented by Formula I or an agriculturally acceptable salt or ester thereof at an application rate a;

Y=effect in percent using (b) an ethylene inhibitor, or an agriculturally acceptable salt or ester thereof at an application rate b;

E=expected (calculated) effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation. Likewise, with respect to the desired crop, if the observed effect is lower than the value E calculated according to the Colby equation, then a synergistic effect is present according to the Colby equation with respect to safening.

In some embodiments, the compositions and methods disclosed herein are synergistic as defined by the Colby equation. In some embodiments, the joint action of the ethylene inhibitor and the compound represented by Formula (I) or an agriculturally acceptable salt or ester thereof can result in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the observed effect for undesired vegetation is at least 1%, at least 2%, at least 3%, at least 4%, at least 5%, at least 10%, at least 15%, at least 20%, at least 25%, at least 27%, at least 30% or at least 32% greater than the expected effect (E) calculated according to the Colby equation (e.g., an observed effect of 96% would be 4% greater than a calculated effect (E) of 92%). In some embodiments, for undesired vegetation, the difference (DO) between 100% and the observed effect is at least 5%, at least 10%, at least 15%, at least 20%, at least 25%, at least 30%, at least 35%, at least 40%, at least 45%, or at least 50% less than the difference (DE) between 100% and the expected effect (E) calculated according to the Colby equation (e.g., an observed effect of 96% would produce a DO of 4%, a calculated effect (E) of 92% would produce a DE of 8%, and DO would be 50% less than or half of DE). In some embodiments, E is greater than X+Y.

In some embodiments, the weight ratio of (a) the ethylene inhibitor in g ai/ha to (b) a compound represented by Formula I or an agriculturally acceptable salt or ester thereof in g ai/ha, that is sufficient to induce a synergistic herbicidal effect is at least 1:1000 (e.g., at least 1:950, at least 1:900, at least 1:850, at least 1:800, at least 1:750, at least 1:700, at least 1:650, at least 1:600, at least 1:550, at least 1:500, at least 1:450, at least 1:400, at least 1:350, at least 1:300, at least 1:250, at least 1:200, at least 1:150, at least 1:100, at least 1:90, at least 1:80, at least 1:70, at least 1:60, at least 1:50, at least 1:45, at least 1:40, at least 1:35, at least 1:30, at least 1:25, at least 1:20, at least 1:18, at least 1:16, at least 1:15, at least 1:14, at least 1:12, at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, at least 100:1, at least 150:1, at least 200:1, at least 250:1, at least 300:1, or at least 350:1). In some embodiments, the weight ratio of (a) the ethylene inhibitor in g ai/ha to (b) a compound represented by Formula I or an agriculturally acceptable salt or ester thereof in g ai/ha, that is sufficient to induce a synergistic herbicidal effect is less than 400:1 (e.g., less than 350:1, less than 300:1, less than 250:1, less than 200:1, less than 150:1, less than 100:1, less than 90:1, less than 80:1, less than 70:1, less than 60:1, less than 50:1, less than 45:1, less than 40:1, less than 35:1, less than 30:1, less than 25:1, less than 20:1, less than 18:1, less than 17:1, less than 16:1, less than 15:1, less than 10:1, less than 9:1, less than 8:1, less than 7:1, less than 6:1, less than 5:1, less than 4:1, less than 3:1, less than 2:1, less than 1:1, less than 1:2, less than 1:3, less than 1:4, less than 1:5, less than 1:6, less than 1:7, less than 1:8, less than 1:9, or less than 1:10, less than 1:15, less than 1:20, less than 1:30, less than 1:40, less than 1:50, less than 1:60, less than 1:70, less than 1:80, less than 1:90, less than 1:100, less than 1:150, less than 1:200, less than 1:250, less than 1:300, less than 1:350, less than 1:400, less than 1:450, less than 1:500, less than 1:600, less than 1:700, less than 1:800, less than 1:900, or less than 1:950).

The weight ratio of (a) the ethylene inhibitor to (b) a compound represented by Formula I or an agriculturally acceptable salt or ester thereof that is sufficient to induce a synergistic herbicidal effect can range from any of the minimum ratios described above to any of the maximum values described above. In some embodiments, the weight ratio of (a) the ethylene inhibitor in g ai/ha to (b) a compound represented by Formula I or an agriculturally acceptable salt or ester thereof in g ai/ha, that is sufficient to induce a synergistic herbicidal effect is from 1:1000 to 400:1. In some embodiments, the weight ratio (a) the ethylene inhibitor in g ai/ha to (b) a compound represented by Formula I or an agriculturally acceptable salt or ester thereof in g ai/ha can be in any of the following ranges: from 1:800 to 400:1, 1:900 to 350:1, 1:800 to 300:1, 1:500 to 200:1, 1:200 to 100:1, 1:60 to 50:1, 1:50 to 45:1, 1:40 to 20:1, 1:10 to 50:1, 1:20 to 5:1, 1:20 to 1:1, 1:16 to 2.5:1, 1:15 to 10:1, 1:12 to 2.5:1, 1:10 to 10:1, 1:8 to 5:1, 1:6.4 to 5:1, 1:5 to 2:1, 1:5 to 1:1, 1:1 to 1:5, 1:1 to 1:20, 1:6.4 to 5:4 or 1:2.5 to 6.5:1.

In some embodiments, the active ingredients consist of (a) and (b), i.e., the composition does not include a herbicidal active ingredient in addition to (a) and (b). In some embodiments, the active ingredients consist of (a) and (b), and the composition further comprises a safener.

The present disclosure also relates to formulations of the compositions and methods disclosed herein. In some embodiments, the formulation can be in the form of a single package formulation including both (a) an ethylene inhibitor and (b) a compound represented by Formula I or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains compound (a) and optionally at least one additive while the other package contains compound (b) and optionally at least one additive. In some embodiments of the two-package formulation, the formulation including compound (a) and optionally at least one additive and the formulation including compound (b) and optionally at least one additive are mixed before application and then applied simultaneously. In some embodiments, the mixing is performed as a tank mix (i.e., the formulations are mixed immediately before or upon dilution with water). In some embodiments, the formulation including compound (a) and the formulation including compound (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of compound (a) and compound (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, self-emulsifying formulations, pastes, dusts, and materials for spreading or granules.

In some embodiments, (a) the ethylene inhibitor and/or (b) a compound represented by Formula (I) or an agriculturally acceptable salt or ester thereof, is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of 10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be an additional pesticide, fungicide, insecticide, plant growth regulator, or combinations thereof. In some embodiments, the additive can be diluted in water or can be concentrated. In some embodiments, the additive is added sequentially. In some embodiments, the additive is added simultaneously. In some embodiments, the additive is premixed with the compound represented by Formula I or an agriculturally acceptable salt or ester thereof. In some embodiments, the additive is premixed with the ethylene inhibitor or agriculturally acceptable salt or ester thereof.

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: 4-CPA; 4-CPB; 4-CPP; 2,4-D; 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, other 4-aminopicolinic acid based herbicides, such as those described in U.S. Pat. Nos. 7,314,849 and 7,432,227 to Balko, et al., 4-amino-6-(heterocyclic)picolinates and 6-amino-2-(heterocyclic)pyrimidine-4-carboxylates, such as those described in U.S. Published Application No. 2014/0274695, aminopyralid, amiprofos, aminotriazole, amitrole, ammonium sulfamate, ammonium thiocyanate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, benthiocarb, bentazon, benzadox, benzfendizone, benzipram, benzobicyclon, benzofenap, benzofluor, benzoylprop, benzthiazuron, bicyclopyrone, bifenox, bilanafos, bispyribac such as bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlormequat, chlorimuron, chlornitrofen, chloropon, chlorotoluron, chloroxuron, chloroxynil, chlorpropham, chlorsulfuron, chlorthal, chlorthiamid, chlortoluron, cinidon, cinmethylin, cisanilide, clethodim, cliodinate, clodinafop, clofop, clomazone, clomeprop, cloprop, cloproxydim, clopyralid, cloransulam such as cloransulam-methyl, CMA, copper sulfate, CPMF, CPPC, credazine, cresol, cumyluron, cyanatryn, cyanazine, cycloate, cyclopyralid, cyclopyrimorate, cyclosulfamuron, cycloxydim, cycluron, cyhalofop such as cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxasulfone, fenteracol, fenthiaprop, fentrazamide, fenuron, ferrous sulfate, flamprop, flazasulfuron, florasulam, fluazifop, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, fumiclorac, furyloxyfen, gibberellic acid, glufosinate, glyphosate, halosafen, halosulfuron, haloxydine, haloxyfop, hexachloroacetone, hexaflurate, hexazinone, imazamethabenz, imazamox, imazapic, imazapyr, imazaquin, imazethapyr, imazapic, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifos, karbutilate, ketospiradox, lactofen, lenacil, linuron, MAA, MAMA, MCPA, MCPA amines, MCPB, mecoprop, medinoterb, mefenacet, mefluidide, mesoprazine, mesosulfuron, mesotrione, metam, metamifop, metamitron, metazosulfuron, metazachlor, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, 1-naphthaleneacetic acid, naproanilide, napropamide, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prohexadione, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron, pyrazoxyfen, pyribenzoxim, pyributicarb, pyriclor, pyridafol, pyridate, pyriftalid, pyrimisulfan, pyrithiobac, pyroxasulfone, pyroxsulam, quinclorac, quinmerac, quinoclamine, quinonamid, quizalofop, rhodethanil, rimsulfuron, saflufenacil, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiameturon, thiazafluron, thiazopyr, thidiazimin, thidiazuron, thiencarbazone, thifensulfuron, thiobencarb, tiocarbazil, tioclorim, topramezone, tralkoxydim, tri-allate, triafamone, triasulfuron, triaziflam, tribenuron, tricamba, triclopyr, triclopyr amines, tridiphane, trietazine, trifloxysulfuron, trifluralin, triflusulfuron, trifop, trifopsime, trihydroxytriazine, trimeturon, tripropindan, tritac tritosulfuron, vernolate, xylachlor, and salts, esters, optically active isomers, and mixtures thereof.

In some embodiments, the additional pesticide, fungicide, insecticide, or plant growth regulator is provided in a premixed formulation with (a), (b), or combinations thereof. In some embodiments, the compound represented by Formula I or an agriculturally acceptable salt or ester thereof is provided in a premixed formulation with an additional pesticide, fungicide, insecticide, or plant growth regulator. In some embodiments, the ethylene inhibitor is provided in a premixed formulation with an additional pesticide, fungicide, insecticide, or plant growth regulator.

In some embodiments, the additive is an RNAi. The RNAi may have plant and pest modifying activities beneficial to the activity of the compositions comprising a synergistic herbicidally effective amount of (a) an ethylene inhibitor (e.g. 1-methylcyclopropene), and (b) a compound of Formula I, or an agriculturally acceptable salt or ester thereof.

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, C9-C11 alkylpolyglycoside or less, phosphate alcohol ethoxylate or less, natural primary alcohol (C12-C16) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG(400) dioleate-99.

In some embodiments, the additive is a safener that is an organic compound leading to better crop plant compatibility when applied with a herbicide. In some embodiments, the safener itself is herbicidally active. In some embodiments, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet, cyometrinil, cyprosulfamide, daimuron, dichlormid, dicyclonon, dietholate, dimepiperate, disulfoton, fenchlorazole, fenclorim, flurazole, fluxofenim, furilazole, harpin proteins, isoxadifen, jiecaowan, jiecaoxi, mefenpyr, mephenate, naphthalic anhydride, 2,2,5-trimethyl-3-(dichloroacetyl)-1,3-oxazolidine, 4-(dichloroacetyl)-1-oxa-4-azaspiro [4.5]decane, oxabetrinil, R29148, N-phenyl-sulfonylbenzoic acid amides, and salts, esters, optically active isomers, and mixtures thereof. In some embodiments, the safener can be cloquintocet or an ester or salt or ester thereof, such as cloquintocet (mexyl). In some embodiments, the safener can be dichlormid.

Exemplary surfactants (e.g., wetting agents, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamin B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to NMR spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

In some embodiments, a method of controlling undesirable vegetation which comprises contacting the vegetation or the locus thereof with or applying to the soil or water to limit the emergence or growth of vegetation any of the compositions is disclosed herein.

The compositions disclosed herein can be applied pre-emergence (before the emergence of undesirable vegetation) or post-emergence (i.e., during and/or after emergence of the undesirable vegetation). If desired, the compositions can be applied as an in-water application.

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to limit the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, herbicidal activity is exhibited by the compounds of the mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. In some embodiments, the undesirable vegetation is controlled in a monocot or row crop. Exemplary crops include, but are not limited to, wheat, barley, triticale, rye, teff, oats, corn, maize, *sorghum*, rice, milo, *Brachiaria*, sugarcane, vegetables, soybean, cotton, sunflower, canola, oilseed, rapeseed, tree and vine crops, perennial crops, plantation crops, and range land (e.g., pasture grasses), roadsides, IVM (industrial vegetation management, such as railroads, tank farms, parking lots, around buildings, ditchbanks, etc), and forestry. In some embodiments, the compositions and methods disclosed herein can be used for controlling undesired vegetation in rice, corn, or wheat. In some embodiments, the composition can be applied as a directed spray in, for example, vegetables, soybean, cotton, sunflower, canola, oilseed, rapeseed, tree and vine crops, perennial crops, plantation crops.

The compositions and methods disclosed herein can be used for controlling undesired vegetation in non-crop areas. Exemplary non-crop areas include, but are not limited to, turfgrass, pastures, grasslands, rangelands, fallow land, rights of way, aquatic settings, wildlife management areas, or rangeland. In some embodiments, the compositions and methods disclosed herein can be used for non-selective control of undesirable vegetation in industrial vegetation management (IVM) or for utility, pipeline, roadside, tank farms, parking lots, around buildings, ditchbanks, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used in turfgrass (e.g., residential, industrial, and institutional lawns), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenic fungi owing to genetic engineering or breeding. In some embodiments, the compositions and methods disclosed herein can be used in crop plants that are resistant to attack by insects owing to genetic engineering or breeding. In some embodiments, the compositions and methods described herein can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, photosystem inhibitors (I and II), triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, photosynthesis inhibitors, triazines, and bromoxynil tolerant crops possessing single, multiple or stacked traits conferring tolerance to single or multiple chemistries and/or multiple modes of action. In some embodiments, the undesirable vegetation can be controlled in a crop that is ACCase-tolerant, ALS tolerant, or a combination thereof. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

The compositions and methods may be used in controlling undesirable vegetation in crops possessing agronomic stress tolerance (including but not limited to drought, cold, heat, salt, water, nutrient, fertility, pH), pest tolerance (including but not limited to weeds, insects, fungi and pathogens) and crop improvement traits (including but not limited to yield; protein, carbohydrate, or oil content; protein, carbohydrate, or oil composition; plant stature and plant architecture).

In some embodiments, the compositions and methods provided herein are utilized to control undesirable vegetation consisting of grass, broadleaf and sedge weeds, or a combination thereof.

In some embodiments, the compositions and methods provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SCPJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AM:VICO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morning glory, IPOHE), *Lindernia dubia* (L.) Pennell (low false pimpernel, LIDDU), *Monochoria korsakowii* Regel & Maack (*monochoria*, MOOKA), *Monochoria vaginalis* (Burm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (mild smartweed, POLHP), *Rotala indica* (Willd.) Koehne (Indian toothcup, ROTIN), *Sagittaria* species, (arrowhead, SAGSS), *Sesbania exaltata* (Raf) Cory/Rydb. Ex Hill (hemp *sesbania*, SEBEX), or *Sphenoclea zeylanica* Gaertn. (gooseweed, SPDZE).

In some embodiments, the compositions and methods provided herein are utilized to control undesirable vegetation in oilseed rape, canola, drilled crops, and cereal crops. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Lolium rigidum* (rigid ryegrass, LOLRI), *Lolium multiflorum* subsp. *Gaudini* (annual ryegrass, LOLMG), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compositions and methods provided herein are utilized to control undesirable vegetation found in row crops, tree and vine crops, perennial crops, and non-crop areas. In certain embodiments, the undesirable vegetation is *Alopecurus myosuroides* Huds. (blackgrass, ALOMY), *Amaranthus palmeri* S. Wats. (Palmer amaranth, AMAPA), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R. D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbur, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Sesbania exaltata* (Raf.) Cory/Rydb. Ex Hill (hemp *sesbania*, SEBEX), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred *anoda*, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC., *Spermacoce alata* Aubl. or *Spermacoce latifolia* (broadleaf buttonweed, BOILF), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (horseweed, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morning glory, IAQTA), *Ipomoea hederacea* (L.) Jacq. (ivyleaf morning glory, IPOHE), *Ipomoea lacunosa* L. (white morning glory, IPOLA), *Lactuca serriola* L./Torn. (prickly lettuce, LACSE), *Portulaca oleracea* L. (common purslane, POROL), *Richardia* species (pusley, RCHSS), *Salsola tragus* L. (Russian thistle, SASKR), *Sida* species (*sida*, SIDSS), *Sida spinosa* L. (prickly *sida*, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the compositions and methods provided herein are utilized to control undesirable vegetation in range and pasture. In certain embodiments, the undesirable vegetation is *Amaranthus palmeri* S. Wats. (Palmer amaranth, AMAPA), *Ambrosia artemisiifolia* L. (common ragweed, AMBEL), *Ambrosia trifida* L. (giant ragweed, AMBTR), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Conyza canadensis* (L.) Cronq. (horseweed, ERICA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Salsola tragus* L. (Russian thistle, SASKR), *Sesbania exaltata* (Raf) Cory/Rydb. Ex Hill (hemp *sesbania*, SEBEX), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compositions and methods provided herein are utilized to control undesirable vegetation found in row crops and vegetable crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (Western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morning glory, IAQTA), *Ipomoea hederacea* (L.) Jacq. (ivyleaf morning glory, IPOHE), *Ipomoea lacunosa* L. (white morning glory, IPOLA), *Lactuca serriola* L./Torn. (prickly lettuce, LACSE), *Portulaca oleracea* L. (common purslane, POROL), *Sida spinosa* L. (prickly *sida*, SIDSP),

*Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, the combination of the compositions disclosed herein can be used for controlling *Echinochloa crus-galli* (L.) P. Beauv. (barnyard grass, ECHCG), *Cyperus esculentus* L. (yellow nutsedge, CYPES), *Digitaria sanguinalis* (L.) Scop. (large crabgrass, DIGSA), *Echinochloa colonum* (L.) LINK (junglerice, ECHCO) and *Ipomoea hederacea* (L.) Jacq. (ivyleaf morning glory, IPOHE).

The herbicidal compositions described herein can be used to control herbicide resistant or tolerant weeds. The methods employing the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinyl-thiobenzoates, triazolopyrimidines, sulfonylaminocarbonyl-triazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenyl-phthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxy-genase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

By way of non-limiting illustration, examples of certain embodiments of the present disclosure are given below.

EXAMPLES

Evaluation of Foliar Applications of 2-arylpyridine Carboxylic Acid Ester and 1-methylcyclopropene for Synergistic Weed Control Seeds or nutlets of the desired test plant species were planted in a soil matrix prepared by mixing a sandy loam soil (28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 $cm^2$. When required, to ensure good germination and healthy plants, a fungicide treatment and/or other chemical or physical treatment was applied. The plants were grown for 10-22 days in a greenhouse with an approximate 14 h photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the second or third true leaf stage.

Herbicide treatments consisted of the benzyl ester of 4-amino-3-chloro-5-fluoro-6-(4-chloro-2-fluoro-3-methoxy-phenyl) pyridine-2-carboxylic acid alone (Formula II), formulated as an SC (suspension concentrate), and 1-methylcyclopropene alone (3.8% w/w ai), and in combination. The compounds were applied on an active ingredient basis.

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) Agri-Dex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 $m^2$ at a spray height of 18 inches (43 cm) above average plant canopy height. Control plants were sprayed in the same manner with the solvent blank. The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to complete growth of the undesired vegetation and 100 corresponds to complete prevention of the undesired vegetation. Colby's equation was used to determine the herbicidal effects expected from the mixtures. The combinations tested, ratios employed, plant species tested, and results are included in Table 1 below.

TABLE 1

Synergistic activity of foliar-applied of Formula (II) benzyl ester and 1-methylcyclopropene evaluated at 20-21 days after application to weeds in a foliar-applied rice cropping system.

| Weed (Bayer Code) | Formula (II) benzyl ester g ai/ha | % Visual Weed Control | 1-methylcyclopropene g ai/ha | % Visual Weed Control | Formula (II) benzyl ester + 1-methylcyclopropene Observed % Visual Weed Control | Colby Predicted % Visual Weed Control |
|---|---|---|---|---|---|---|
| CYPES | 0 | — | 5 | — | 0 | — |
| CYPES | 8 | 70 | 5 | — | 95 | 70 |
| CYPES | 16 | 88 | 5 | — | 95 | 88 |
| CYPES | 32 | 73 | 5 | — | 100 | 73 |
| DIGSA | 0 | — | 5 | 0 | — | — |
| DIGSA | 16 | 23 | 5 | 0 | 35 | 23 |
| DIGSA | 32 | 30 | 5 | 0 | 50 | 30 |
| DIGSA | 0 | — | 10 | 0 | — | — |
| DIGSA | 16 | 23 | 10 | 0 | 45 | 23 |
| DIGSA | 32 | 30 | 10 | 0 | 40 | 30 |
| DIGSA | 0 | — | 20 | 0 | — | — |
| DIGSA | 16 | 23 | 20 | 0 | 40 | 23 |
| DIGSA | 32 | 30 | 20 | 0 | 35 | 30 |
| ECHCG | 0 | — | 5 | 0 | — | — |
| ECHCG | 32 | 83 | 5 | 0 | 95 | 83 |
| ECHCG | 0 | — | 10 | 0 | — | — |
| ECHCG | 32 | 83 | 10 | 0 | 90 | 83 |
| ECHCG | 0 | — | 20 | 0 | — | — |
| ECHCG | 32 | 83 | 20 | 0 | 95 | 83 |
| IPOHE | 0 | — | 5 | 0 | — | — |
| IPOHE | 16 | 18 | 5 | 0 | 50 | 18 |
| IPOHE | 0 | — | 10 | 0 | — | — |
| IPOHE | 16 | 18 | 10 | 0 | 40 | 18 |

Percent Visual Weed Control = 0-100 scale, where 0 = no control and 100 = complete control.
CYPES = yellow nutsedge, *Cyperus esculentus* L.
DIGSA = large crabgrass, *Digitaria sanguinalis* (L.) Scop.
ECHCG = barnyard grass, *Echinochloa crus-galli* (L.) P. Beauv.
IPOHE = ivyleaf morning glory, *Ipomoea hederacea* (L.) Jacq.
g ai/ha = grams active ingredient per hectare

TABLE 2

Synergistic activity of foliar-applied of Formula (II) benzyl ester and 1-methylcyclopropene evaluated at 20-21 days after application to weeds in a foliar-applied rice cropping system.

| Weed (Bayer Code) | Formula (II) benzyl ester g ai/ha | % Visual Weed Control | 1-methylcyclopropene g ai/ha | % Visual Weed Control | Formula (II) benzyl ester + 1-methylcyclopropene Observed % Visual Weed Control | Colby Predicted % Visual Weed Control |
|---|---|---|---|---|---|---|
| CYPES | 8 | 70 | 5 | 0 | 95 | 70 |
| CYPES | 16 | 88 | 5 | 0 | 95 | 88 |
| CYPES | 32 | 73 | 5 | 0 | 100 | 73 |
| DIGSA | 8 | 13 | 2 | 0 | 28 | 13 |
| DIGSA | 16 | 28 | 2 | 0 | 18 | 28 |
| DIGSA | 32 | 33 | 2 | 0 | 40 | 33 |
| DIGSA | 8 | 13 | 4 | 0 | 15 | 13 |
| DIGSA | 16 | 28 | 4 | 0 | 43 | 28 |
| DIGSA | 32 | 33 | 4 | 0 | 38 | 33 |
| DIGSA | 8 | 20 | 5 | 0 | 10 | 20 |
| DIGSA | 16 | 23 | 5 | 0 | 35 | 23 |
| DIGSA | 32 | 30 | 5 | 0 | 50 | 30 |
| DIGSA | 8 | 20 | 10 | 0 | 30 | 20 |
| DIGSA | 16 | 23 | 10 | 0 | 45 | 23 |
| DIGSA | 32 | 30 | 10 | 0 | 40 | 30 |

TABLE 2-continued

Synergistic activity of foliar-applied of Formula (II) benzyl ester and 1-methylcyclopropene evaluated at 20-21 days after application to weeds in a foliar-applied rice cropping system.

| Weed (Bayer Code) | Formula (II) benzyl ester | | 1-methylcyclopropene | | Formula (II) benzyl ester + 1-methylcyclopropene | |
|---|---|---|---|---|---|---|
| | g ai/ha | % Visual Weed Control | g ai/ha | % Visual Weed Control | Observed % Visual Weed Control | Colby Predicted % Visual Weed Control |
| DIGSA | 8  | 20 | 20 | 0 | 30 | 20 |
| DIGSA | 16 | 23 | 20 | 0 | 40 | 23 |
| DIGSA | 32 | 30 | 20 | 0 | 35 | 30 |
| ECHCG | 8  | 40 | 2  | 0 | 63 | 40 |
| ECHCG | 16 | 63 | 2  | 0 | 75 | 63 |
| ECHCG | 32 | 90 | 2  | 0 | 93 | 90 |
| ECHCG | 8  | 40 | 4  | 0 | 48 | 40 |
| ECHCG | 16 | 63 | 4  | 0 | 75 | 63 |
| ECHCG | 32 | 90 | 4  | 0 | 95 | 90 |
| ECHCG | 8  | 63 | 5  | 0 | 60 | 63 |
| ECHCG | 16 | 78 | 5  | 0 | 90 | 78 |
| ECHCG | 32 | 83 | 5  | 0 | 95 | 83 |
| ECHCG | 8  | 63 | 10 | 0 | 60 | 63 |
| ECHCG | 16 | 78 | 10 | 0 | 75 | 78 |
| ECHCG | 32 | 83 | 10 | 0 | 90 | 83 |
| ECHCG | 8  | 63 | 20 | 0 | 65 | 63 |
| ECHCG | 16 | 78 | 20 | 0 | 90 | 78 |
| ECHCG | 32 | 83 | 20 | 0 | 95 | 83 |
| ECHCO | 8  | 50 | 2  | 0 | 40 | 50 |
| ECHCO | 16 | 50 | 2  | 0 | 80 | 50 |
| ECHCO | 32 | 80 | 2  | 0 | 85 | 80 |
| ECHCO | 8  | 50 | 4  | 0 | 65 | 50 |
| ECHCO | 16 | 50 | 4  | 0 | 80 | 50 |
| ECHCO | 32 | 80 | 4  | 0 | 95 | 80 |
| IPOHE | 16 | 25 | 2  | 0 | 40 | 25 |
| IPOHE | 32 | 35 | 2  | 0 | 45 | 35 |
| IPOHE | 16 | 25 | 4  | 0 | 30 | 25 |
| IPOHE | 32 | 35 | 4  | 0 | 48 | 35 |
| IPOHE | 16 | 18 | 5  | 0 | 50 | 18 |
| IPOHE | 32 | 48 | 5  | 0 | 55 | 48 |
| IPOHE | 16 | 18 | 10 | 0 | 40 | 18 |
| IPOHE | 32 | 48 | 10 | 0 | 45 | 48 |

Percent Visual Weed Control = 0-100 scale, where 0 = no control and 100 = complete control.
CYPES = yellow nutsedge, *Cyperus esculentus* L.
DIGSA = large crabgrass, *Digitaria sanguinalis* (L.) Scop.
ECHCG = barnyard grass, *Echinochloa crus-galli* (L.) P. Beauv.
IPOHE = ivyleaf morning glory, *Ipomoea hederacea* (L.) Jacq.
g ai/ha = grams active ingredient per hectare The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a synergistic herbicidally effective amount of:
   (a) 1-methylcyclopropene; and
   (b) a compound of Formula I, or an agriculturally acceptable salt or ester thereof:

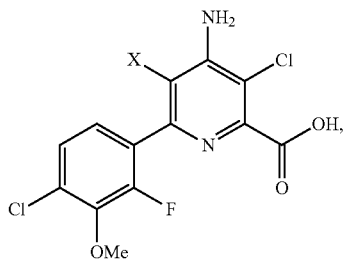

wherein X is hydrogen or fluorine.

2. The composition of claim 1, wherein (b) is a methyl or benzyl ester of Formula (I).

3. The composition of claim 1, wherein the weight ratio of (a) in g ai/ha to (b) in g ai/ha is from 1:16 to 2.5:1.

4. The composition of claim 1, further comprising an additional herbicide including aminocyclopyrachlor, cyhalofop-butyl, fenoxaprop, metamifop, profoxydim, azimsulfuron, bensulfuron, bispyribac-sodium, cloransulam-methyl, diclosulam, florasulam, glufosinate, glyphosate, halosulfuron, imazamox, imazethapyr, imazapic, imazosulfuron, metazosulfuron, penoxsulam, pyroxsulam, pyrazosulfuron, 2,4-D, aminopyralid, clopyralid, fluroxypyr, MCPA, paraquat, picloram, triclopyr, bentazon, saflufenacil, or an agriculturally acceptable salt or ester thereof, and combinations thereof.

5. The composition of claim 1, further comprising a herbicidal safener.

6. The composition of claim 1, further comprising an RNAi.

7. The composition of claim 1, wherein the active ingredients in the composition consist of (a) and (b).

8. A method of controlling undesirable vegetation which comprises applying to vegetation or an area adjacent the vegetation or applying to soil or water to limit the emergence or growth of vegetation a composition comprising a synergistic herbicidally effective amount of (a) 1- methylcyclopropene, and (b) a compound of Formula I, or an agriculturally acceptable salt or ester thereof:

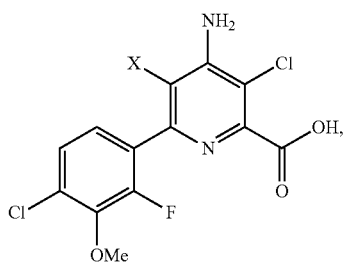

wherein X is hydrogen or fluorine.

9. The method of claim 8, wherein (a) and (b) are applied postemergence to the undesirable vegetation.

10. The method of claim 8, wherein (b) is a methyl or benzyl ester of Formula (I).

11. The method of claim 8, wherein the undesirable vegetation includes a grass weed, broadleaf weed, or sedge weed.

12. The method of claim 8, wherein the undesirable vegetation includes a weed from the genus *Cyperus, Echinochloa, Digitaria,* or *Ipomoea.*

13. The method of claim 8, wherein the undesirable vegetation is controlled in a monocot crop selected from rice, wheat, barley, oats, corn, maize, *sorghum*, milo, Brachiaria, pastures, sugarcane, and turfgrass.

14. The method of claim 8, wherein the undesirable vegetation is controlled in vegetables, soybeans, cotton, sunflower, canola, oilseed, rapeseed, tree and vine crops, perennial crops, and plantation crops.

15. The method of claim 8, wherein the undesirable vegetation is controlled in non-crop areas selected from roadsides, industrial vegetation management, and forestry.

16. The method of claim 8, wherein the undesirable vegetation is controlled in turfgrass, golf courses, parks, cemeteries, athletic fields, and sod farms.

17. The method of claim 8, wherein the (a) is applied at a rate of 2 to 20 g ai/ha.

18. The method of claim 8, wherein the (b) is applied at a rate of 8 to 32 g ai/ha.

19. The method of claim 8, wherein the undesirable vegetation comprises a herbicide resistant or tolerant weed, wherein the resistant or tolerant weed is a biotype with resistance or tolerance to single or multiple herbicides, single or multiple chemical classes, single or multiple herbicide modes-of-action or via single or multiple resistance mechanisms.

20. A method of modifying crop growth and yield comprising applying to the crop or an area adjacent the crop or applying to soil or water to modify growth and yield of the crop a composition comprising a synergistic herbicidally effective amount of (a) 1-methylcyclopropene, and (b) a compound of Formula I, or an agriculturally acceptable salt or ester thereof:

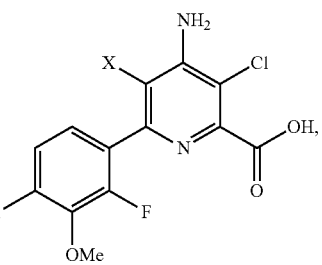

wherein X is hydrogen or fluorine, wherein (a) and (b) are each added in an amount sufficient to provide a crop modifying effect.

* * * * *